United States Patent [19]

Bernstein et al.

[11] 4,018,764
[45] Apr. 19, 1977

[54] UREYLENEBIS METHYL-PHENYLENE-CARBONYL-BIS-DIHYDRO-2-OXO-NAPHTHOXAZINE DISULTONIC ACIDS

[75] Inventors: Seymour Bernstein, New City, N.Y.; Robert Herman Lenhard, Paramus, N.J.; Milton David Heller, New City, N.Y.

[73] Assignee: American Cyanamid Company, Stamford, Conn.

[22] Filed: May 10, 1976

[21] Appl. No.: 684,695

[52] U.S. Cl. .......................... 260/246 R; 424/248.5
[51] Int. Cl.$^2$ ............ C07D 265/00; C07D 273/00; C07D 295/00
[58] Field of Search ................. 260/246 R; 424/248

[56] References Cited

OTHER PUBLICATIONS

J. Chem. Soc., 3068–3079 (1927), Balaban and King—Trypanocidal Action.

Primary Examiner—Albert T. Meyers
Assistant Examiner—D. W. Robinson
Attorney, Agent, or Firm—Jack W. Richards

[57] ABSTRACT

Ureylenebis[methyl-phenylene carbonyl]-bis-[dihydro-2-oxo-naphth-oxazine-disulfonic acids] and salts thereof useful as complement inhibitors.

2 Claims, No Drawings

UREYLENEBIS METHYL-PHENYLENE-CARBONYL-BIS-DIHYDRO-2-OXO-NAPHTHOXAZINE DISULTONIC ACIDS

BACKGROUND OF THE INVENTION

The present invention resides in the concept of certain ureylenebis[methyl-phenylene carbonyl]bis-[dihydro-2-oxo-naphth-oxazine-disulfonic acids] and salts thereof useful as inhibitors of the complement system of warm-blooded animals.

The term "complement" refers to a complex group of proteins in body fluids that, working together with antibodies or other factors, play an important role as mediators of immune allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of sub-units designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935–938 (1968); *Scientific American*, 229, (No. 5), 54–66 (1973) *Medical World News*, October 11, 1974, pp. 53–58, 64–66; *Harvey Lectures*, 66, 75–104 (1972); *The New England Journal of Medicine*, 287, 489–495; 545–549; 592–596; 642–646 (1972); *The Johns Hopkins Med. J.*, 128, 57–74 (1971); and *Federation Proceedings*, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969).

A variety of substances have been disclosed as inhibiting the complement system, i.e., as complement inhibitors. For example, the compounds 3,3'-ureylene-bis-[6-(2-amino-8-hydroxy-6-sulfo-1-naphthylazo)]-benzenesulfonic acid tetrasodium salt (chlorazol fast pink), heparin and a sulphated dextran have been reported to have an anticomplementary effect, *British Journal of Experimental Pathology*, 33, 327–339 (1952). The compound 8,8'-[ureylene[m-phenylenecarbonylimino (4-methyl-m-phenylene)carbonylimino]]di-1,3,5-naphthalenetrisulfonic acid, hexasodium (Suramin Sodium) as a competitive inhibitor of the complement system, *Clin. Exp. Immunol.*, 10, 127–138 (1972). German Pat. No. 2,254,893 or South African Pat. No. 727,923 discloses certain 1-(diphenylmethyl)-4-(3-phenylallyl)piperazines useful as complement inhibitors. U.S. Pat. No. 3,897,434 discloses certain pyrazolo[1,5c]quinazolin-5(6H)-ones useful as complement inhibitors. The compound m-[m-(p-nitrophenylureido)phenoxypropoxy]benzamidine is also known as a complement inhibitor, *Immunology*, 26, 819 (1974). Other chemical compounds having complement inhibiting activity are disclosed in, for example, *Journal of Medicinal Chemistry*, 12, 415–419; 902–905; 1049–1056 (1969); *Canadian Journal of Biochemistry*, 47, 547–552 (1969); *The Journal of Immunology*, 104, 279–288 (1970); *The Journal of Immunology*, 106, 241–245 (1971) and *The Journal of Immunology*, 111, 1061–1066 (1973).

It has been reported that the known complement inhibitors epsilon-aminocapronic acid, Suramin Sodium and tranexamic acid have been used with success in the treatment of hereditary angioneurotic edema, a disease state resulting from an inherited deficiency or lack of function of the serum inhibitor of the activated first compound of complement (C1 inhibitor), *The New England Journal of Medicine*, 286, 808–812 (1972); *Allergol, Et. Immunopath*, II, 163–168 (1974); and *J. Allergy Clin. Immunol.*, 53, No. 5, 298–302 (1974).

SUMMARY OF THE INVENTION

This invention is concerned with certain ureylenebis[methyl-phenylene carbonyl]bis-[dihydro-2-oxo-naphth-oxazine-disulfonic acids] and salts, and their use, which can be represented by general formula (I):

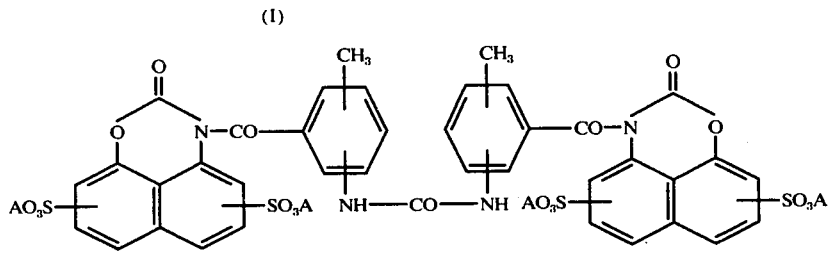

wherein A is hydrogen, alkali metal or alkaline earth, with the proviso that A is identical in the same compound. Preferably, A is sodium or potassium.

A compound of particular interest within formula (I) is the compound 3,3'-Ureylenebis[4-methyl-1,3-phenylene carbonyl] -bis[2,3-dihydro-2-oxo-naphth[1,8-de]-1,3-oxazine-5,8-disulfonic acid] tetrasodium salt which can be represented by the formula (II):

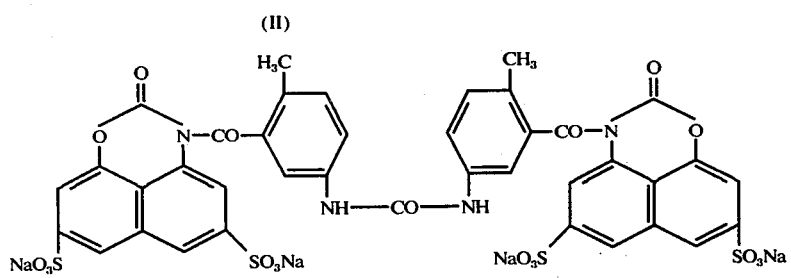

It has now been discovered that a representative compound encompassed within formulae (I) and (II) interacts with the complement reaction sequence, thereby inhibiting complement activity in body fluids.

This invention is also concerned with a method of inhibiting the complement system in a body fluid, such as blood serum, which comprises subjecting body fluid complement to the action of an effective complement inhibiting amount of a compound encompassed within formulae (I) and (II) hereinabove. The method of use aspect of this invention is also concerned with a method of inhibiting the complement system in a warm-blooded animal which comprises internally administering to said animal an effective inhibiting amount of a compound encompassed with formula (I) and (II) hereinabove. Body fluid can include blood, plasma, serum, synovial fluid, cerebrospinal fluid, or pathological accumulations of fluid as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoflobinuria, hereditary angioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture on transport mediums.

The compounds of the invention may be prepared by reacting the appropriate 4-hydroxy-5-(nitro-toluamido)-naphthalenedisulfonic acid, di-salt, as illustrated in Example 1, with hydrogen in the presence of palladium as charcoal to obtain the corresponding 4-(amino-toluamido)-5-hydroxy-naphthalenedisulfonic acid, di-salt, which in turn is treated as illustrated in Example 2, to obtain the corresponding ureylenebis[-methyl-phenylene carbonyl]-bis-[dihydro-2-oxo-naphth-oxazine-disulfonic] tetra-salt. Acidification produces the free acid. The closest known reference to the compounds of the invention is *J. Chem. Soc.*, 3068 (1927).

DETAILED DESCRIPTION OF THE INVENTION

The following examples will serve to illustrate the invention in more detail.

Example 1

4-(5-Amino-o-toluamido)-5-hydroxy-2,7-naphthalenedisulfonic acid, disodium salt

A mixture of 25.0 g of 4-hydroxy-5-(5-nitro-o-toluamido)-2,7-naphthalenedisulfonic acid, disodium salt, 200 ml of distilled water and 2.5 g of 10% palladium on charcoal is hydrogenated in a Parr shaker for 5 hours at room temperature during which time 12 pounds of hydrogen is absorbed. The mixture is heated on a steam bath and is filtered through diatomaceous earth to remove the catalyst. The filter is washed with hot water and the filtrate is then evaporated to about 100 ml of in vacuo at 55°–60° C with formulation of crystals after standing at room temperature overnight. The product of the example is collected by filtration and is washed with absolute ethyl alcohol followed by ether then is oven dried at 120° C.

Example 2

3,3'-{Ureylenebis[(6-methyl-3,1-phenylene)carbonyl]}-bis[2,3-dihydro-2-oxonaphth[1,8-de]-1,3-oxazine-5,8-disulfonic acid], tetrasodium salt To a stirred solution of 10.0 g of 4-(5-amino-o-toluamido)-5-hydroxy-2,7-naphthalenedisulfonic acid, disodium salt (prepared as described in Example 1) and 21.4 g of anhydrous sodium carbonate in 250 ml of water is bubbled in phosgene for 1 hour at room temperature. Then an additional 21.4 g of sodium carbonate is added and phosgenation is continued for 1 hour and 25 minutes. The resulting mixture is neutralized with 16.5 g of sodium carbonate and is filtered and the filtrate is set aside. The precipitate is washed with a small amount of water then is oven dried at 120° C for several hours to give the product of the example.

Example 3

Preparation of Compressed Tablet

| Ingredient | mg/Tablet |
|---|---|
| Active Compound | 0.5–500 |
| Dibasic Calcium Phosphate NF | qs |
| Starch USP | 40 |
| Modified Starch | 10 |
| Magnesium Stearate USP | 1–5 |

Example 4

Preparation of Compressed Tablet-Sustained Action

| Ingredient | mg/Tablet |
|---|---|
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

Example 5

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

Example 6

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

Example 7

Preparation of Oral Liquid (Elixir)

| Ingredient | % W/V |
|---|---|
| Active Compound | 0.05–5 |
| Alcohol USP | 12.5 |

Example 7-continued

Preparation of Oral Liquid (Elixir)

| Ingredient | % W/V |
|---|---|
| Glycerin USP | 45.0 |
| Syrup USP | 20.0 |
| Flavoring Agent | qs |
| Purified Water qs ad | 100.0 |

Example 8

Preparation of Oral Suspension (Syrup)

| Ingredient | % W/V |
|---|---|
| Active Compound as Aluminum Lake, Micronized (acid equivalent) | 0.05–5 |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

Example 9

Preparation of Injectable Solution

| Ingredient | % W/V |
|---|---|
| Active Compound | 0.05–5 |
| Benzyl Alcohol NF | 0.9 |
| Water for Injection | 100.0 |

Example 10

Preparation of Injectable Oil

| Ingredient | % W/V |
|---|---|
| Active Compound | 0.05–5 |
| Benzyl Alcohol | 1.5 |
| Sesame Oil qs ad | 100.0 |

Example 11

Preparation of Intra-Articular Product

| Ingredient | Amount |
|---|---|
| Active Compound | 2–20 mg |
| NaCl (physiological saline) | 0.9% |
| Sodium Carboxymethylcellulose | 1–5% |
| pH adjusted to 5.0–7.5 | |
| Water for Injection qs to | 100% |

Example 12

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NE | 0.9 |
| HCl to pH 6–8 | qs |
| Water for Injection qs ad | 100.0 |

The compounds of this invention may be administered internally, e.g., orally, or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every 6 hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, discalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action to the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animals subjects, each unit containing a predetermined quantity of active component calculated to produce the desired therapeutic effect in association with the required pharmaceutical diluent carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of a representative compound of this invention has been demonstrated by one or more of the following identified tests: (i) Test, Code 026 (C1 inhibitor). This test measures the ability of activated human fluid phase human C2 in the presence of C4 and appropriate dilutions of the test compound. An active inhibitor protects C2 from C1 and C4; (ii) Test, Code 035 (C3-C9 inhibitor). This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor). In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test. Here, the well known complement dependent lesion, Forsssman vasculitis, is produced in guinea pigs by intradermal injection of rabbit anti-Forssman anti-serum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test. Lethal shock is produced in guinea pigs by an i.v. injection of anti-Forssman antiserum and the harmonic mean death time of treated guinea pigs is compared with that of simultaneous controls; (vi) Complement Level Reduction Test. In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test. Here, appropriate amounts of the test compound are added to a pool of guinea serum in vitro, after which the undiluted serum capillary tube assay referred to above is run. The concentration of compound inhibiting 50% is reported.

Table I shows that a representative compound of the invention possess complement inhibitory activity.

TABLE I
Biological Activities

| Compound | Assay Results In Vitro | | |
|---|---|---|---|
| | 026* | 035 | 036 |
| 3,3'-{Ureylenebis[(6-methyl-3,1-phenylene)-carbonyl]}[2,3-dihydro-2-oxonaphth[1,8--de]-1,3-oxazine-5,8-disulfonic acid], tetra-sodium salt | 3** | 2 | Neg. |

*Test identified by code herein.
**Numbers represent activity in wells, a serial silution assay, higher well number indicates higher activity. The serial dilutions are two-fold.

We claim:
1. A compound selected from those of the formula:

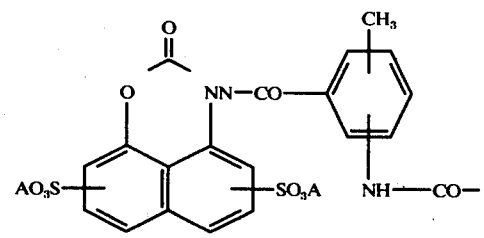

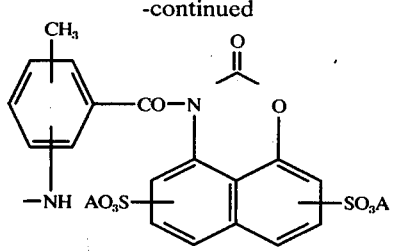
-continued wherein A is hydrogen, alkali metal or alkaline earth, with the proviso that A is identical in the same compound.

2. A compound according to claim 1, of the formula:

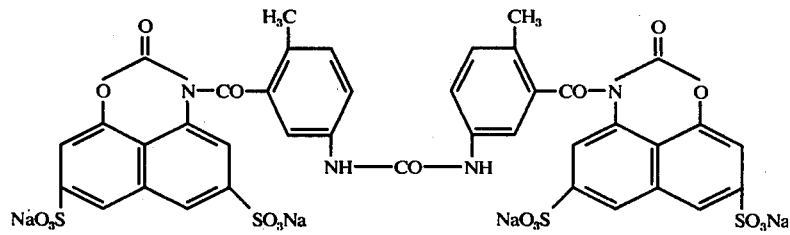

* * * * *

UNITED STATES PATENT OFFICE
CERTIFICATE OF CORRECTION

Patent No. 4,018,764        Dated April 19, 1977

Inventor(s) Seymour Bernstein et al.

It is certified that error appears in the above-identified patent and that said Letters Patent are hereby corrected as shown below:

Claim 1, formula, left-hand side should appear as shown below:

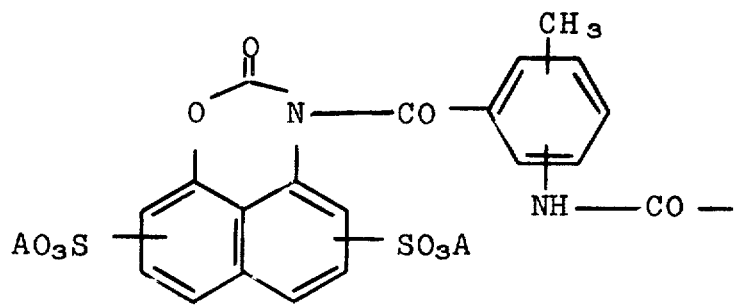

Signed and Sealed this

Twenty-eighth Day of June 1977

[SEAL]

Attest:

RUTH C. MASON
*Attesting Officer*

C. MARSHALL DANN
*Commissioner of Patents and Trademarks*